United States Patent [19]
O'Boyle

[11] Patent Number: 5,125,069
[45] Date of Patent: Jun. 23, 1992

[54] BLOOD WARMER

[75] Inventor: Matthew O'Boyle, Somers, Conn.

[73] Assignee: Netherlands Health Sciences, Lake Charles, La.

[21] Appl. No.: 455,075

[22] Filed: Dec. 22, 1989

[51] Int. Cl.[5] .............................. F24H 1/10
[52] U.S. Cl. .................... 392/465; 392/470; 392/471; 165/46; 165/146; 165/147; 165/170; 128/400; 128/399
[58] Field of Search ............... 219/299, 295, 296, 297, 219/298, 301–309, 328, 330, 331, 336, 338, 506, 501, 497, 505, 10.55 M, 10.55 F; 165/46, 146, 147, 170; 128/214, 399, 400; 392/465, 470, 471

[56] References Cited

U.S. PATENT DOCUMENTS

| | | | |
|---|---|---|---|
| 3,293,868 | 12/1966 | Gonzalez | 62/3 |
| 3,612,059 | 10/1971 | Ersek | 128/399 |
| 4,314,143 | 2/1982 | Bilstad et al. | 219/497 |
| 4,532,414 | 7/1985 | Shah et al. | 219/308 |
| 4,574,876 | 3/1986 | Aid | 165/46 |
| 4,707,587 | 11/1987 | Greenblatt | 219/299 |
| 4,735,609 | 4/1988 | Comeau et al. | 604/114 |
| 4,782,212 | 11/1988 | Bakke | 219/299 |
| 4,801,777 | 1/1989 | Auerbach | 219/10.55 |
| 4,847,470 | 11/1989 | Bakke | 219/299 |

Primary Examiner—Bruce A. Reynolds
Assistant Examiner—Tu Hoang
Attorney, Agent, or Firm—Fitch, Even, Tabin & Flannery

[57] ABSTRACT

Apparatus for changing the temperature of an infusible liquid from a first temperature to a second predetermined temperature. The apparatus includes a receiver assembly for changing the temperature of the liquid. The apparatus also includes a cartridge to be received in the assembly and which defines an enclosed passageway for movement of the fluid. The cartridge has a first end, a second end, a liquid inlet disposed adjacent the first end, a liquid output disposed adjacent the second end, and a first wall extending between the ends and made of a material having good heat transfer properties. The assembly includes a thermoelectric heat pump, and a slot is provided for releasably receiving the cartridge so that the heat pump engages the wall of the cartridge. The assembly also includes a temperature sensor engaging the wall adjacent the ouptut and an electric circuit which is responsive to the temperature sensor for controlling operation of the heat pump so that the liquid exiting the cartridge is at the predetermined temperature.

25 Claims, 4 Drawing Sheets

BLOOD WARMER

The invention is directed to the warming of refrigerated blood, and other transfusable liquids such as fresh frozen plasma or packed red blood cells prior to their infusion into medical patients.

BACKGROUND OF THE INVENTION

Whole blood is refrigerated for storage to between 4° C. to 10° C. for its storage life which ranges between 1-2 months. Other blood products such as plasma, including fresh frozen plasma, and serum may also be refrigerated for storage. The finite storage life of blood precludes stockpiling large amounts of blood and limits the stored supply to blood collected within two months of their use. To further complicate the storage problem, refrigerated blood and blood products must be warmed to body temperature before administration to patients, and once blood has been warmed it cannot be chilled and stored again. In order to avoid wasting blood, various devices have been devised so that blood and blood products can be warmed during transfusion. For the sake of simplicity, the terms blood and blood warmer have been used in describing the invention and liquid warmed therein; however, it is to be understood that the present invention may be used to warm or cool other transfusable liquids, e.g., fresh-frozen plasma, plasma, serum, peritoneal fluid, or any other liquid for which it is desirable to bring the liquid to a specified temperature before infusion to a patient.

Many transfusions are of the gravity type which are performed by attaching a tube continuous with a transfusion bottle or bag suspended approximately 1 M above the patient to a vena puncture site on the patient. The elevated position of the transfusion container relative to the patient provides gravitational pressure on the blood. The flow rate of a gravity transfusion is controlled by applying a screw clamp to the plastic tubing. Depending on the patient's needs, typical gravity transfusion flow rates vary in range from 3 ml/minute. to 30 ml/minute. Gravity transfusion flow rates can be varied rapidly within these ranges by adjusting the screw clamp in response to a change in the patient's medical condition.

Other transfusion methods are used when a patient requires significantly higher transfusion rates. In some cases, manual compression of bolus chambers is used to force a small quantity of blood into a patient at high flow rates. Some surgical procedures, such as thoracic surgery, require bolus transfusions to be performed periodically during surgery. When higher flow rates are required, mechanical pumps may be used to create transfusion flow rates as high as 1 liter per minute. Similarly, heart/lung machines, used during prolonged cardiac surgery, pump, oxygenate, and warm or cool blood while returning it to the patient at high flow rates. In all of these high flow rate transfusion methods, liquid flow rate is often varied quickly in response to the patient's changing medical condition.

It is therapeutically advantageous for traumatized patients to receive blood as close to 37° C. as possible because the significantly cooler or warmer transfusions can cause the patient additional stress. Transfusion with under-warmed bloods may result in hypothermia. Such transfusions can cause a varying degree of hypothermia depending on the volume of blood transfused and its temperature. General anesthetic also causes some degree of hypothermia as a normal side effect. While it is desirable to avoid hypothermia in severely traumatized patients, hypothermia is particularly dangerous if the traumatized patient's body temperature decreases below 35° C. because of the increased risk of ventricular fibrillation. The risk of ventricular fibrillation is heightened during major surgery because both general anesthetic and transfusions are usually required and both can contribute to hypothermia.

While hypothermia is to be generally avoided in traumatized patients, the condition is advantageous in some situations, e.g., to combat a febrile condition or to reduce blood flow and respiration during cardiac surgery. During cardiac surgeries, hypothermia is commonly induced by circulating the patient's blood through a cooling apparatus so that the patient's heart beat is slowed.

Hypothermia is not the only problem in the transfusion warming art, over-warmed blood can be equally harmful to transfusion patients as under-warmed blood. Two possible problems occur with overheating blood, i.e., hemolysis of red blood cells or blood coagulation. Hemolysis can occur when blood temperature attains 42° C. for a significant period of time. Hemolysis can result in poor oxygen carrying capacity and renal difficulties in the patient. Coagulation can be even more dangerous. Blood coagulation may occur when blood temperatures significantly exceeds 42° C. for a significant period of time. Coagulation can result in fluid path occlusions in the warming device or transfusion tubing, or if coagulated blood particles enter the patient, thrombosis may occur. Thus, it can readily seen that the ideal transfusion warmer is one which can maintain a constant blood discharge temperature of 37° C.

Unfortunately, no currently available transfusion warmers can cheaply and efficiently maintain relatively constant discharge temperatures during periods of changing blood flow rates. Procedures such as thoracic surgery lucidly illustrate the problems in the transfusion warming art. During thoracic surgery, small boluses of blood are transfused to the patient by manual compression of a bolus chamber which contains between 10-25 ml of blood so that approximately 10 ml of blood is transfused to the patient at very high liquid flow rates. When serial boluses are required, currently available warming device cannot rapidly and efficiently increase the amount of heat transferred to the blood per unit time it flows through the warmer so that later boluses are discharged at a nearly constant temperature. Thus, in most of the currently available devices increasingly under-warmed blood may be discharged to the patient after successive boluses. After boluses are no longer required, the transfusion rate is drastically decreased and most warming devices overwarm the blood remaining in their liquid chamber because their active heating elements continue to radiate and conduct heat after the heating element is deactivated in response to decreased liquid flow rate. The amount of time required for the device to return discharge temperature to the 37° C. after a change in liquid flow rate is defined as the device's thermal response time. It can be readily seen that the shorter the thermal response time, the less under-warmed or over-warmed blood will be discharged to the patient.

The problems of rapid response time and thermal overshoot were recognized by U.S. Pat. No. 4,707,587 issued to Greenblatt. The Greenblatt apparatus attempts to solve the response time and thermal overshoot problems by using air as the medium of heat conduction. However, the Greenblatt apparatus is both complicated and expensive for dealing with these problems. Unfortunately, using gas as a thermal conduction medium requires the device to include complicated and relatively expensive mechanical devices for operation such as a blood input pressurizer, a gaseous heat exchanger, and electric fans.

U.S. Pat. No. 3,293,868 issued to Gonzalez describes a device designed primarily for cooling peritoneal fluid infusions using a Peltier effect thermocouple as a cooling source (see col. 11 54-59 and col. 11 9-22). The device may alternately be used for warming such fluids by manually activating a switch which reverses the current in the thermocouples. The device is designed so that thermocouples are maintained at constant temperature surrounding thermoplastic conduit through which the liquid flows. Heat is reversibly exchanged from the thermocouple to the fluid contained within a thermoplastic tubing.

Another approach to warming blood is illustrated U.S Pat. No. 4,782,212 issued to Bakke which also exemplifies the prior art's failure to adequately deal with changing blood flow rates. Bakke describes an electrical resistance warmer composed of a thin metal flattened conduit sandwiched between thick metal buffer blocks surrounded by resistance heaters. The current in the resistance heaters is cycled in an attempt to maintain a relatively constant temperature of 37° C. in the buffer blocks. The thickness of the metal buffer blocks prevents rapid response to changing blood flow rates because of long thermal path between the heat source and fluid.

Other problems in the transfusion art are presented by the container which holds the blood while heat is transferred to it. Existing transfusion warmers require air traps downstream from the blood warmer so that air bubbles will not create emboli in the patient. Because air traps require technical training and manual dexterity to properly install, it would be advantageous to make them unnecessary. Because increased liquid flow distance within the container allows a blood warmer to decrease its heating element temperatures, and the prior art taught that lower element temperatures lessen the chance of a dangerous over-temperature conditions, most prior art transfusion containers had labyrinth internal structures. Labyrinth internal structures are more likely to trap air bubbles in their complicated structure and cause substantial turbulence in the liquid flow. Turbulence should be avoided in blood infusions because turbulence can cause damage or lysis of red blood cells.

Additional problems in the transfusion art are created by mobile transfusions required in medical emergencies. During such emergencies, transfusions are often begun at the scene of the injury or during transportation to medical facilities. Military corpsman, paramedics, and ambulance attendants often provide emergency transfusions in ambulances or medical evacuation helicopters. For these mobile transfusions a small portable transfusion warmer is desirable.

Further, most prior art warmers require relatively large amounts of A.C. power which make them impractical for mobile use since sufficient A.C. power is not typically available in the field or on board the medical transportation.

An additional problem in the transfusion art is created by transferring patients between areas of a hospital while transfusing chilled blood. In many emergency room situations, a patient must be transferred to the operating theatre quickly while continuing an infusion of chilled blood. If a warmer is using A.C. power, the power cord must be extended to move the patient while continuing blood warming or the cord may be unplugged. Thus, it would be advantageous if the blood warmer power supply could be switched from A.C. to D.C. for a short period so that the patient could be moved without interrupting the blood warming, and there would be no need for a long power cord.

SUMMARY OF THE INVENTION

Important aspects and objects of the invention are described below. One object of the present invention is to provide an efficient, portable, blood warming or cooling device in which the amount of heat transferred to or from the blood rapidly varies in response to blood temperature so that a nearly constant discharge temperature is maintained. An important aspect of the invention is that the thermoelectric heat pump transfer heats at a rate proportional to the rate cold blood absorbs it so that invention can automatically and efficiently respond to decreased fluid temperature, yet gently coasts into the desired temperature. Another object of the invention is to provide a transfusion warmer which greatly reduces the possibility of thermal overshoot. An important aspect of the invention in achieving this object is that when the blood reaches the desired temperature, the thermoelectric heat pump is switched off and it draws a small amount of heat from the blood. A further object of the invention is to provide a transfusion warmer with a liquid cartridge with small mass, good thermal transfer properties, and a thin wall separating the blood from the thermoelectric heat pump so that the device can rapidly and sensitively transfer heat to or from the thermoelectric heat pump as needed to maintain a substantial constant liquid discharge temperature. Another important object of the invention is to provide a self-purging blood cartridge so that there is no need for a separate air trap with its attendant problems. Another important objective of the invention is to provide a blood warmer with a short, substantially laminar, liquid flow path. A further object of the invention is to provide a portable blood warmer which may be operated by a relatively small direct current battery for use in mobile transfusions. Another important aspect of the invention in achieving portability is the relatively low power consumption per unit heat pumped. A further object of the invention is to provide a blood warmer which may be easily switched from an A.C. power source to a D.C. power source to facilitate patient transfer during infusion. A further object of the invention is to provide a compact, easy to use, blood warmer with either sterilized or disposable blood cartridges. A further object of the invention is to provide a blood warmer which may double as a blood cooler to induce hypothermia when such a state is desirable.

Briefly described, the invention provides a blood warming device that warms blood passing through a cartridge held in intimate thermal contact with a blood warmer supplying heat from at least one thermoelectric heat pump. Blood is supplied to a self-purging liquid cartridge through a liquid inlet and outlet attached to infusion tubes. As the blood fills the cartridge, any air bubbles at the air/liquid boundary are purged from the liquid because the cross-sectional area of enclosed volume is designed to decrease to a minimum at the highest point within the cartridge. The cartridge encloses a wide, thin volume of short path length which contains the blood while heat is transferred to it. At least one high surface area wall defining the cartridge is thin, has good heat transfer properties and low mass, and is maintained in intimate thermal contact with at least one thermoelectric heat pump so that heat is rapidly transferred or absorbed from the blood. The blood warmer contains at least one thermoelectric heat pump which pumps heat to the blood at a rate proportional to the rate the cartridge transfers heat to the blood. As the chilled blood warms in the cartridge, heat transfer from the cartridge wall to the blood slows because of the smaller temperature difference therebetween which causes the thermoelectric heat pump to slow the rate of heat pumping. As blood in the cartridge approaches the desired temperature, the decreased rate of heat pumping helps prevent the blood from overshooting the desired temperature. The blood temperature near the liquid outlet is continuously monitored by a temperature sensor disposed near the outlet. When the blood reaches the desired temperature, the sensor controls operation of the heat pump. As a result of current interruption, the hot and cold sides of the thermoelectric heat pump almost instantaneously reach thermal equilibrium at a temperature below the desired blood temperature causing the thermoelectric heat pump to quickly absorb a small amount of heat from the cartridge which in turn absorbs a like amount from the blood. Thus, the invention will pull back slightly from the desired temperature and thermal overshoot is avoided. After warming, the blood exits the cartridge at the fluid outlet and enters a tube connected to a vena puncture needle for insertion into the patient. Electric power may be supplied to operate the blood warmer as either A.C. or D.C. power source. In the most preferred embodiment, a disposable cartridge is provided which encloses a volume that decreases to a minimum at the outlet. The disposable cartridge is designed to slide into a slot on the blood warmer and displace at least one forward biased temperature sensor and at least one forward biased thermometric heat pump. For the sake of simplicity, the invention will be described for warming blood. It should be recognized that the present invention may act as a blood cooler by merely reversing the direction of the current flowing through the thermoelectric heat pump and by setting the second preset temperature higher than the desired temperature. It should also be recognized that the invention may be used to warm or cool any infusible liquid.

DETAILED DESCRIPTION OF THE PREFERRED EMBODIMENT

Figure 1:
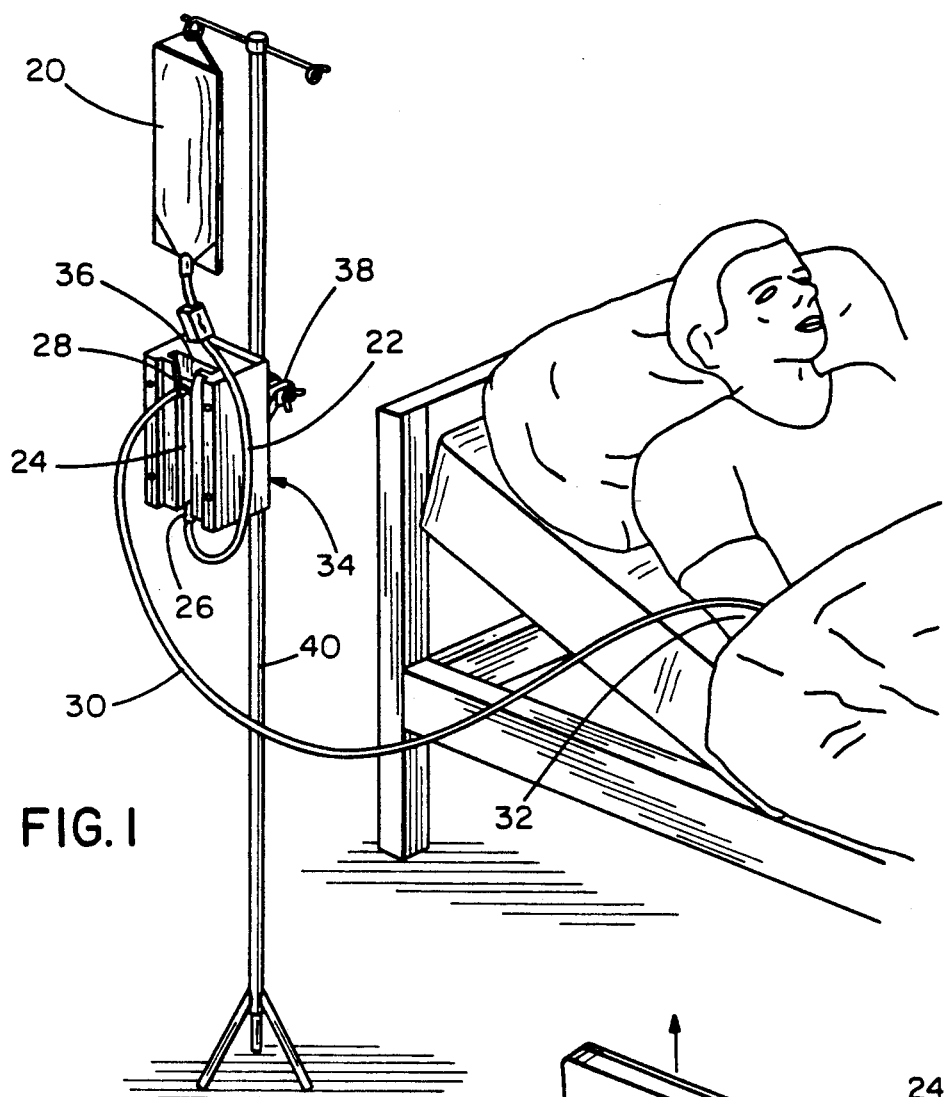
FIG. 1 is a perspective view of blood warming apparatus embodying various aspects of the present invention, including a blood warmer and a disposable cartridge for insertion into the warmer, being employed in the administration of blood to a patient.

Referring to FIG. 1, an infusion bag 20 provides the blood to an inlet tubing 22 which is connected to a cartridge 24 at a liquid inlet 26 so that blood flows through the cartridge 24 exiting the liquid outlet 28 and into the distal tubing 30 which is connected to a vena puncture site on the patient 32. The cartridge 24 is held in intimate thermal contact with a blood warmer or receiver assembly 34 by inserting the cartridge 24 into a T-slot 36 on the blood warmer 34. A clamp 38 holds the blood warmer 34 to an administration stand 40.

Figure 2:
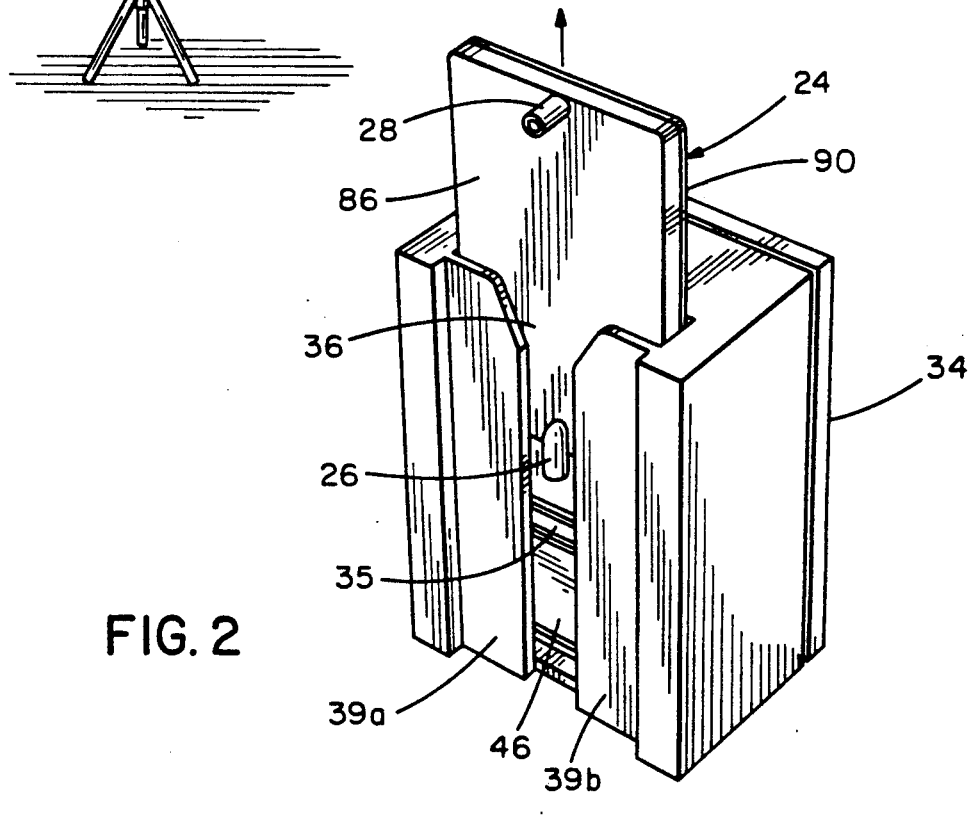
FIG. 2 is a perspective view of the cartridge being removed from the warmer.

Referring to FIG. 2, the cartridge 24 (without tubing 22, 30) is shown partially removed from a T-slot 36 on the blood warmer 34. The cartridge 24 is disposed so that the liquid inlet 26 is toward the bottom of the T-slot and the liquid outlet 28 is near the top. The cartridge 24 can be seen through a central opening 35 of the T-slot 36 which is defined by a pair of plates 39a and 39b aligned in mirror image. The plates 39a and 39b define the front wall of the blood warmer. One of a pair of thermoelectric heat pumps 46 which are deflected rearwardly upon insertion of the cartridge into the warmer, can be seen below cartridge 24. The cartridge 24 is shown in its proper orientation with a first cartridge plate 86 disposed toward the plates 39a and 39b and a second cartridge plate 90 disposed toward the interior of the blood warmer 34 and held in intimate thermal contact with the thermoelectric heat pumps 46.

Figure 3:
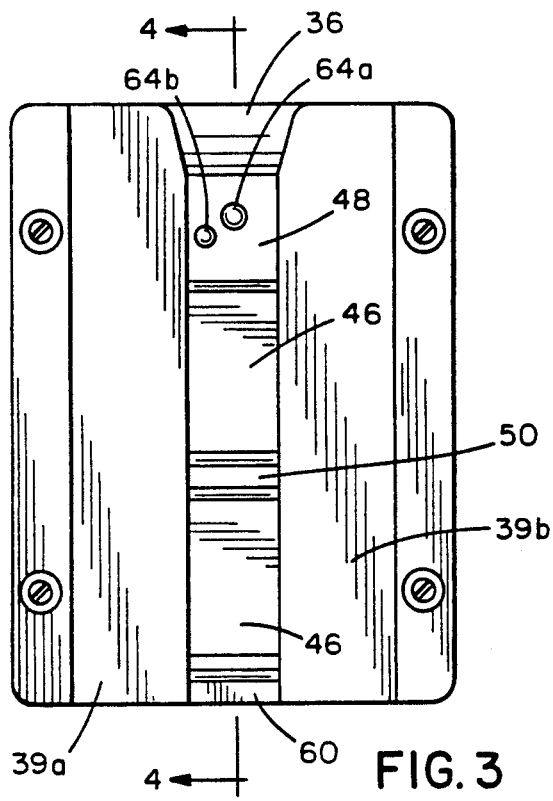
FIG. 3 is a front elevational view of the warmer.
Figure 4:
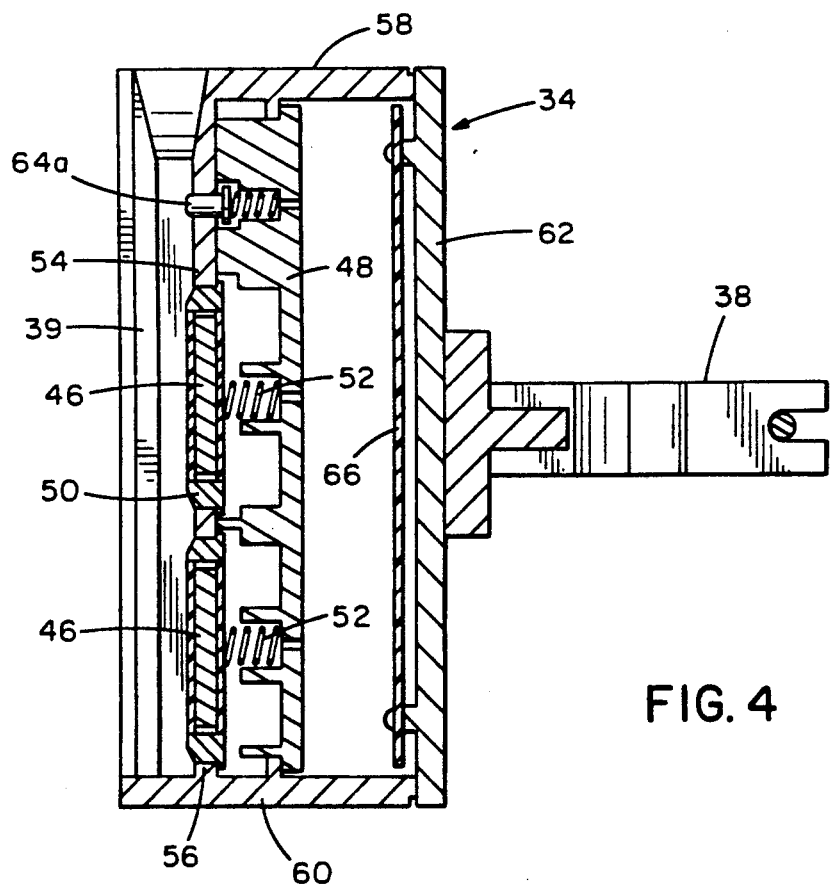
FIG. 4 is a sectional view of the warmer taken generally along the line 4—4 of FIG. 3.
Figure 6:
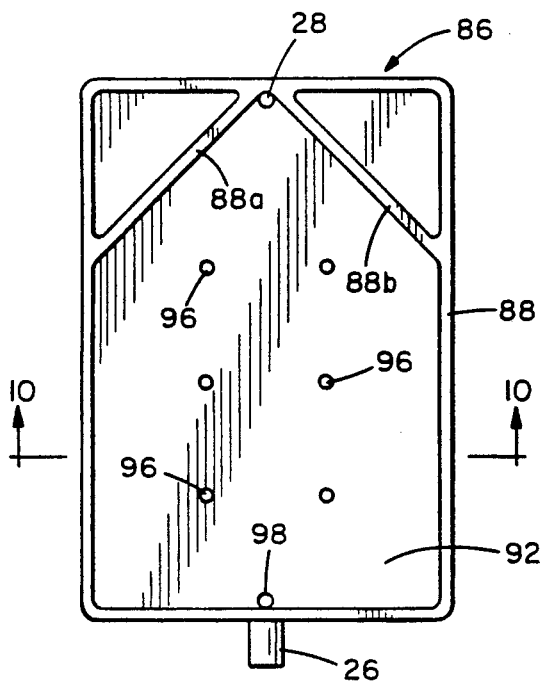
FIG. 6 is a front elevational view of a molded plastic plate comprising half of the cartridge.

Referring to FIGS. 3 and 4, the blood warmer 34 also includes a housing having a back wall 48 with the heat pumps 46 retained on a plate 50 disposed between the housing front wall 39 and the back wall 48. The heat pumps 46 are movable with respect to the front wall between a first position shown in FIG. 4, in which the spacing therebetween is less than the thickness of the cartridge 24, and a second position wherein the cartridge is disposed between the front wall and the heat pumps, as shown in FIG. 1. The blood warmer 34 further includes biasing means in the form of coil extension springs 52 working against the back wall 48 urging the heat pumps toward the first position. Of course, abutments 54 and 56 are provided to limit movement of the plate 50 to the first position. The thermoelectric heat pumps 46 are provided for adding or removing heat from the blood contained in the cartridge 24. The thermoelectric heat pumps 46 may be affixed to plate 50 using epoxy. Suitable thermoelectric heat pumps are commercially available from Materials Electronics Products Corporation of Trenton, N.J. In the preferred embodiment, two thermoelectric heat pumps connected in series have been provided; however, it is recognized that a single larger or more efficient thermoelectric heat pump could be substituted for the two thermoelectric heat pumps in this embodiment.

Referring to FIG. 4, the housing includes a top wall 58 and a bottom wall 60 which closes the base of the slot 36 to limit the extent of insertion of the cartridge into the blood warmer. The blood warmer also includes a back mounting plate 62 which is connected to the clamp 38.

Figure 13:
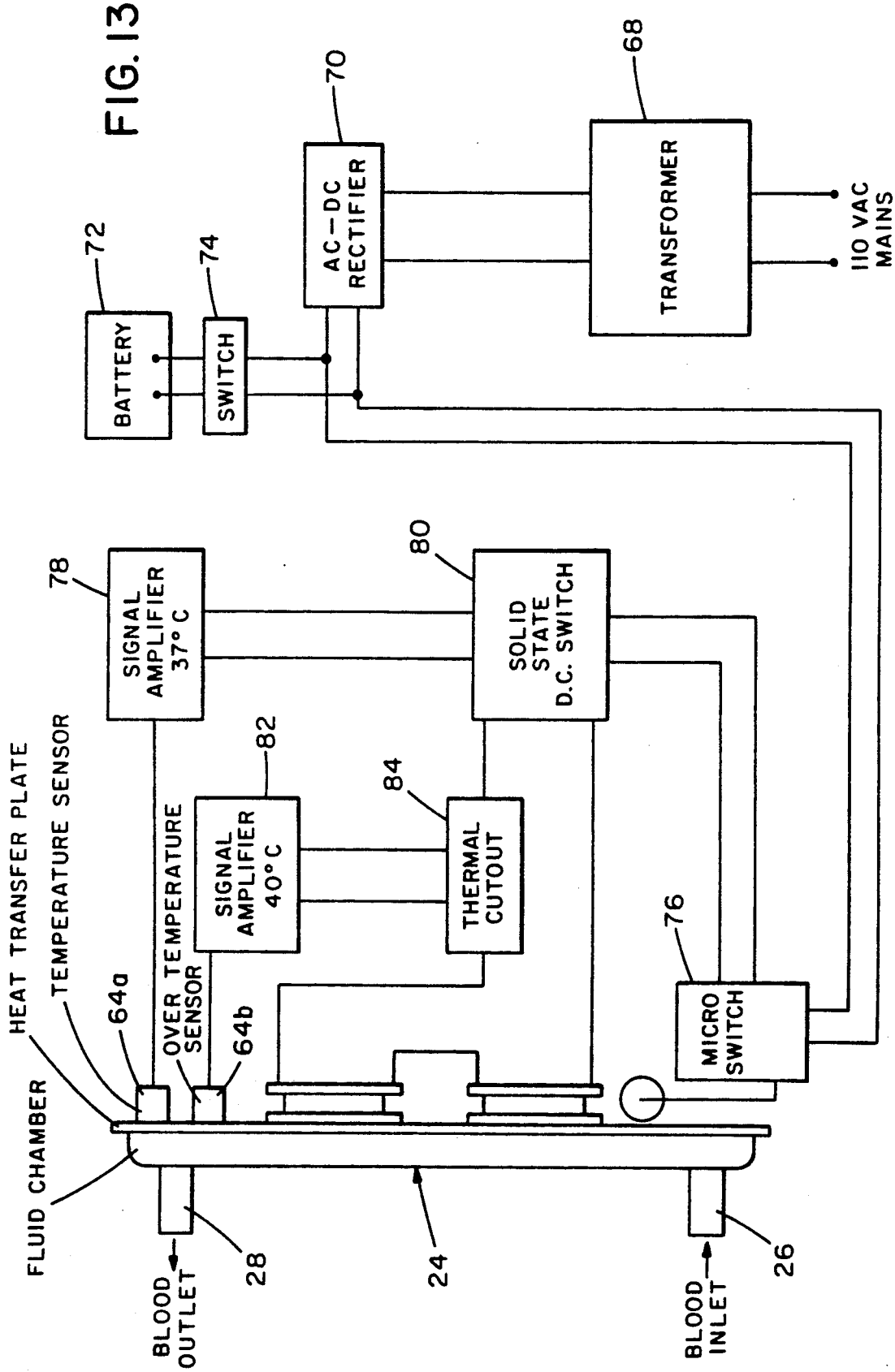
FIG. 13 is a diagram, chiefly in block form, showing various electrical components for supplying power to and controlling operation of the warmer.

Two temperature sensors 64a and 64b are provided for sensing the temperature of the blood near the liquid outlet 26 on the cartridge 24. These sensors are held by back wall 48 and are spring biased so that, while they are deflected rearwardly upon cartridge insertion, they make contact with the cartridge. Referring to FIG. 13, electrical and electronic circuitry for the blood warmer 34 is shown chiefly in block form. Most of this circuitry may be mounted on a circuit board 66 mounted on the back mounting plate 62. The power supply 68 for the heat pumps includes a step down transformer having its primary winding connected to nominal 110 volts, A.C. and its secondary providing an output to a rectifier and pulse shaping network 70 for providing suitable D.C. power for the heat pumps and control circuitry. A battery 72 may be provided and selectively connected by a switch 74 when the warmer 34 is to be used in a portable application or when A.C. power is not available. A limit switch 76 is activated when the cartridge 24 is fully inserted into the blood warmer, to enable power to the heat pumps and the control circuitry. A first sensor 64a sensor provides a signal to an amplifier 78, the output of which is provided to switching circuitry 80 which could include a microprocessor and functions to provide power to the heat pumps until the desired temperature of 37° C. is achieved, and thereafter cycles operation of the heat pumps to cause the temperature of the blood at the outlet 28 to be maintained in a narrow range centered about 37° C. Of course, the switching circuitry can be set to a temperature other than 37° C. Temperature sensor 64b senses an over-temperature condition, e.g., the blood temperature reaching 40° C. The output of sensor 64b is amplified by amplifier 82, the output of which is connected to a thermal output safety switch 84 for disabling the heat pumps when a predetermined over-temperature is achieved. The temperature sensors each have rounded or beveled corners so that the when cartridge 24 is inserted into the T-slot 36, the sensors are pushed back but are forward biased into engagement with the cartridge. The preferred sensors are Analog devices Inc. Model No. AD59 OMH; however, other temperature sensing devices known in the art may be substituted. Similarly, the plate 50 has beveled surfaces to facilitate the passage of the cartridge 24 past the thermoelectric heat pumps during insertion and removal of the cartridge 24 from the T-slot 36.

Figure 5:
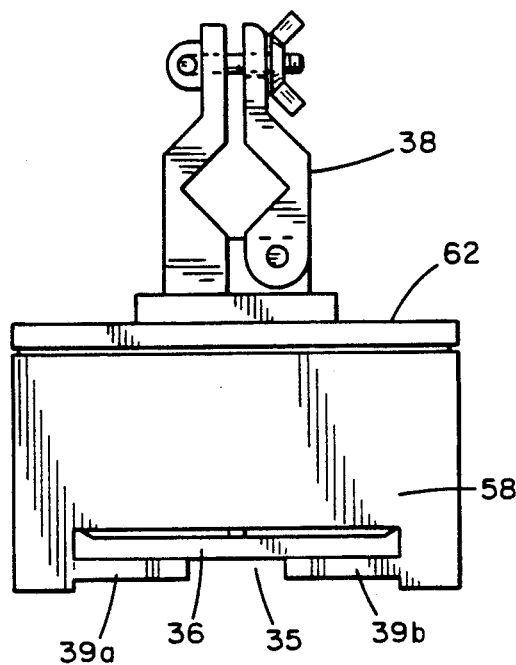
FIG. 5 is plan view of the warmer of FIG. 1.

As shown in FIG. 5, central opening 35 of the T-slot 36 located between plates 39a and 39b allows the liquid inlet 26, the liquid outlet 28 and tubes 22 and 30 connected thereto to protrude perpendicularly from the plane of the cartridge 24 through the central opening 35.

Referring to FIGS. 6–12, a first cartridge plate 86 is provided for defining half of the cartridge 24. The preferred material for the cartridge plate 86 is an injection molded thermoplastic such as polyvinyl chloride, polypropylene, polyethylene, polystyrene or A.B.S., or other injection moldable plastics. Although injection molded plastic is preferred because of its low production cost, it is recognized that stamped or injection molded metal could be substituted for the thermoplastic material of the first cartridge plate 86. The cartridge plate 86 is provided with a raised rim 88 around the outer periphery of the cartridge plate for sealing to a second cartridge plate 90 (best shown in FIGS. 8 and 9) to form the cartridge 24. A recessed center area 92 provides an enclosed volume or liquid passageway 94 when the cartridge plate 86 is bonded to a second cartridge plate 90 to form the cartridge 24 as more clearly seen in FIG. 10. Returning to FIG. 6, rim extensions 88a and 88b are raised an equal distance from recessed area 92 as is the raised rim 88. The rim extensions are provided for decreasing the cross-sectional area of the passageway 94 defining the interior of the cartridge to a minimum at a point within the cartridge so that as the cartridge fills with blood, the rising blood purges air bubbles from the cartridge 24. Alternate embodiments are envisioned wherein a plurality of extensions are provided for decreasing the cross sectional area at more than one point within the cartridge or, the cross-sectional area of the cartridge may be decreased by decreasing the depth of recess 92 to a minimum at one point in the cartridge and adjusting the shape of the second cartridge plate to conform to the change in the depth of the recess.

An array of standoffs 96 is provided for supporting the second cartridge plate 90 defining the other half of the cartridge to prevent collapse or enlargement of the passageway 94. The standoffs 96 are raised an equal distance above the plane of the recess 92 as the rim 88 and rim extensions 88a and 88b. A liquid inlet 26 is provided at the bottom of the cartridge plate for bringing liquid into the passageway 94 defined by the cartridge 24. An opening 98 from the liquid inlet 26 is provided for liquid communication between the inlet 26 and the passageway 94 defined by the cartridge 24. A liquid outlet 28 is provided at the top of the cartridge plate for allowing the fluid to exit the passageway 94. In the most preferred embodiment, the inlet and outlet are female luer lock receptors. However, alternate embodiments are envisioned wherein the inlet and/or outlet are male luer connector adapted to mate with a female luer connector, or male or female connector adapted to mate directly with infusion tubing.

Figure 7:
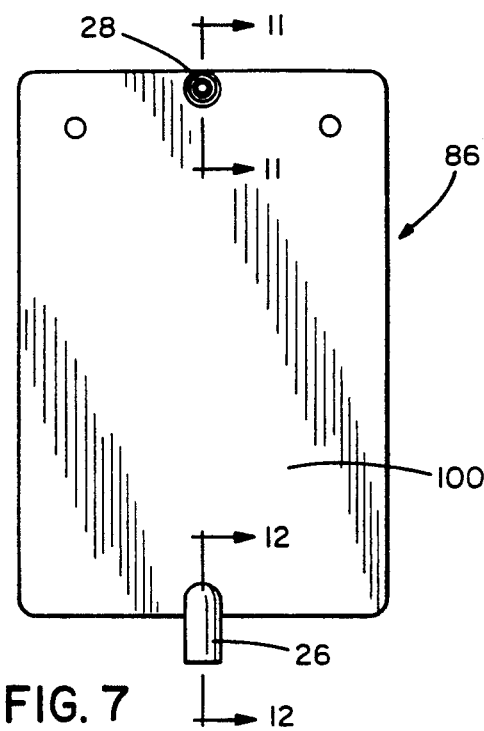
FIG. 7 is a rear elevational view of the molded plastic plate of FIG. 6.

Referring to FIG. 7, the outside surface 100 of the cartridge plate 86 is relatively flat with the exception of the liquid inlet 26 and outlet 28 which extend beyond the plane of the outside surface 100.

Figure 8:
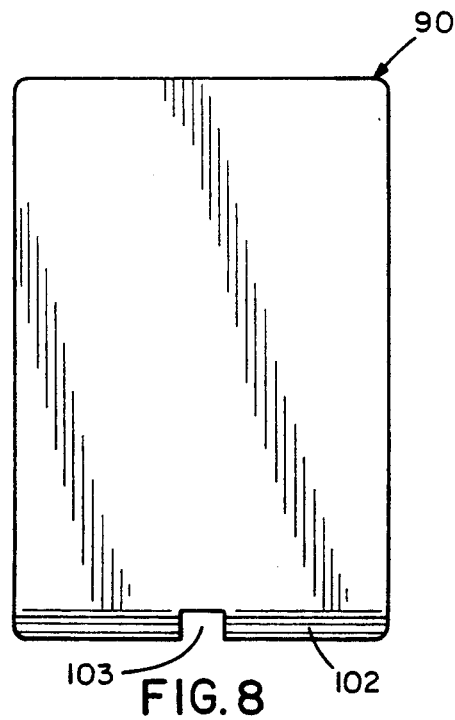
FIG. 8 is a front elevational view of a second plate comprising the other half of the cartridge.

Referring to FIG. 8, a second cartridge plate 90 is provided for sealing with the first cartridge plate 86 and forming the cartridge 24 and for transferring heat to the blood contained within the passageway. The second cartridge plate 90 is made of a material with good heat transfer properties, i.e., a material that is a good conductor and/or a good thermal radiator. In the most preferred embodiment, the material is black anodized aluminum or black anodized aluminum alloys; however, alternate embodiments are envisioned wherein the material is a metal with good heat transfer properties such as copper, zinc, magnesium, or alloys thereof with good thermal transfer properties, or other suitable thermally conductive materials. The surface area of the preferred second plate is about 64 cm$^2$. The second cartridge plate 90 is provided with deflection means in the form of a chamferred leading edge 102 for easing the insertion of the cartridge 24 into the T-slot 36 and past the spring-biased temperature sensors 64a and 64b and the biased thermoelectric heat pumps 46. The chamferred leading edge 102 is provided with a central slot 103 for allowing the liquid inlet 26 to extend past the plane of the chamferred leading edge 102.

Figure 9:
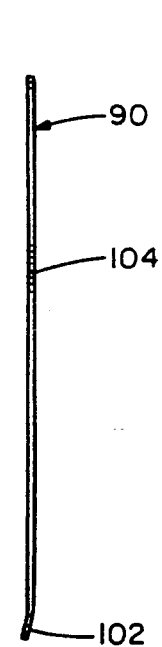
FIG. 9 is a side elevational view of the plate of FIG. 8.

Referring to FIG. 9, the chamferred leading edge 102 can be more easily visualized. The side edge 104 of the second cartridge plate 90 illustrates that the second cartridge plate 90 is thin to promote fast thermal conduction.

Figure 10:
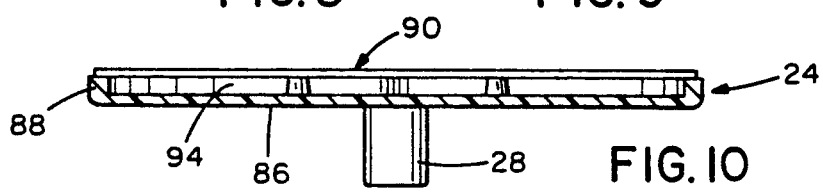
FIG. 10 is a sectional view of the completed cartridge.

Referring to FIG. 10, first cartridge plate 86 is shown attached to second cartridge plate 90 to form cartridge 24. The cartridge plates are preferably attached by solvent or adherent bonding with commercially available materials. The passageway 94 is defined by the first cartridge plate 86, and second cartridge plate 90. The height of the preferred rim 88 is short, preferably between about 0.5 mm and about 2 mm, so that the enclosed volume is slender. The preferred passageway 94 holds at least 10 ml of blood. Liquid outlet 28 can be seen in its preferred orientation, i.e., extending from the plane of the second cartridge plate.

Figure 11:
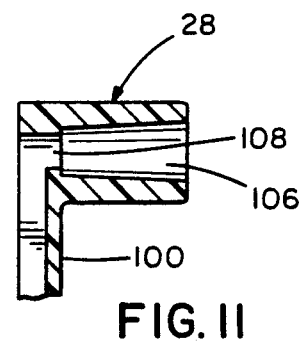
FIG. 11 is a sectional view of the liquid outlet of the cartridge taken along line 11—11 of FIG. 7.

Referring to FIG. 11, the liquid outlet 28 is shown in greater detail. A tapered annular opening 106 is provided for mating with a male luer connector (not shown) affixed to the administration tubing 30. An abutment ring 108 is provided for abutting the male luer connection during insertion into the liquid outlet and for facilitating a good seal between the connector and the outlet.

Figure 12:
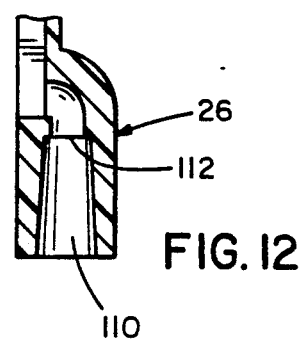
FIG. 12 is a sectional view of the liquid inlet of the cartridge taken along line 12—12 of FIG. 7.

Referring to FIG. 12, the liquid inlet 26 is shown in closer detail. A tapered annular opening 110 is provided for mating with a male luer connector (not shown) on the administration tubing 22. An abutment ring 112 is provided for abutting the male luer connector during insertion and for facilitating a good seal between the connector and the inlet.

Operation of the present invention is as follows. The blood warmer 34 is provided with a source of electrical power either by plugging an electrical cord attached to the transformer 68 into a 110 V A.C. socket or by connecting the battery 72. The cartridge 24 is inserted into the T-slot 36 with its leading edge 102 and fluid inlet 40 inserted first so that they are toward the bottom of the warmer and with first cartridge plate 86 facing outwardly. The chamferred leading edge 102 pushes back forward-biased temperature sensors 64a, 64b and the forward-biased thermoelectric heat pumps 46. The springs urge the sensors and heat pumps into intimate thermal contact with the plate 90. During insertion, the chamferred leading edge moves the operating arm of the limit switch 76 activating the blood warmer's electronics and strikes the bottom wall 60 to complete the insertion process. Upon activation, the temperature sensor will immediately detect a temperature below 37° C. and switching circuitry 80 causes D.C. current to flow to the thermoelectric heat pumps 46.

Liquid tubes 22 and 30 are connected to the fluid inlet 26 and outlet 28, respectively, and the inlet tube 22 and outlet tube 30 protrude through opening 35 in the T-slot 36. Chilled blood is provided by the infusion bag 20 to the administration tubing 22. The blood flows from the tubing 22 into the liquid inlet 26 and begins to fill the passageway 94. As the blood fills the passageway, air bubbles are purged from the cartridge. The temperature sensors 64a and 64b detect the temperature of the second cartridge plate 90 near the outlet 28. The good heat transfer properties of the second cartridge plate, its thinness, and small mass ensure that the temperature sensed at the plate 78 is substantially the temperature of the blood as it is discharged from the cartridge. The temperature sensors 64a and 64b continuously monitor the temperature of the blood exiting the cartridge and provides the information to the switching circuitry 80 and thermal cutout 84, respectively.

While the switching circuitry 80 detects a temperature below the desired temperature, the switch which provides direct current to the thermoelectric heat pump is maintained in the "on" position. The thermoelectric heat pump transfers heat to the blood at a rate proportional to the rate heat is absorbed by the blood. Thus, as chilled blood first enters the cartridge 24, it rapidly absorbs heat and the heat pumps operate at their maximal rate for a given current and voltage. As the blood in the cartridge is warmed, it absorbs heat at a slower rate which causes the heat pumps 46 to pump heat at a slower rate. If blood temperature in the passageway 94 were to drop because of increased liquid flow rate or a cooler blood supply, the blood will absorb heat from the second plate 90 more quickly, and the thermoelectric heat pumps will in turn pump heat at a faster rate. When the sensor 64a detects the desired temperature, the switching circuitry 80 responds by deactivating the switch so that no current is supplied to the thermoelectric heat pumps 46. The opposite sides of thermoelectric heat pumps rapidly reach a thermal equilibrium at a temperature lower than the desired temperature so that a small amount of heat is transferred from the second cartridge plate 90 to the thermoelectric heat pumps and a like amount is transferred from the blood to the second cartridge plate 90. Thus, when the thermoelectric heat pumps are deactivated, the blood temperature will quickly decrease a small amount which decreases the likelihood of an over-temperature condition.

When the temperature sensor 64a indicates that the blood has fallen to a second preset temperature lower than the desired temperature, the switching circuitry 80 reactivates the switch supplying current to the thermoelectric heat pumps. The microprocessor may be preset for a second temperature which is as little as 0.1° C. lower than the desired temperature so that the thermoelectric heat pumps will be cycled on/off quickly to provide a substantially constant discharge temperature. Because the second cartridge plate 90 has low mass, good heat transfer properties, and is thin, the invention rapidly and sensitively transfers heat between the thermoelectric heat pumps and the blood. Thereby, the invention is very sensitive to small changes in sensed blood temperature. The likelihood of an over-temperature condition after a slowing in liquid flow rate is minimized by the low mass of the liquid cartridge, the proportional rate of heat pumping, and the thermal pullback in blood temperature when the heat pump is switched off.

While description of the operation of the invention is in the blood warming mode, those skilled in the art will recognize that the invention may be used for cooling the blood to a desired temperature by reversing the direction of the current in the thermoelectric heat pump and selecting a second preset temperature higher than the desired temperature. For the sake of brevity and clarity, the described embodiment and its operation have been described warming blood, those skilled in the art will recognize that the invention may be used for warming or cooling a wide variety of infusible fluids.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for changing the temperature of an infusible liquid from a first temperature to a second predetermined temperature, said apparatus comprising:
   a receiver assembly for changing the temperature of the liquid; and
   a cartridge to be received in said receiver assembly and defining an enclosed passageway for movement of said fluid, said cartridge having a first end and a second end, a liquid inlet disposed adjacent said first end, a liquid outlet disposed adjacent said second end, and a first wall extending between said ends and of material having good heat transfer properties and which partially defines said passageway,
   said receiver assembly including a thermoelectric heat pump means for transferring to and absorbing heat from said cartridge means for releasably receiving said cartridge so that said heat pump means engages said first wall of said cartridge, temperature sensing means engaging said first wall adjacent said outlet, and electric circuit means responsive to said temperature sensing means for controlling operation of said heat pump means so that the liquid exiting said cartridge is at substantially said predetermined temperature.

2. Apparatus as set forth in claim 1 wherein said cartridge has a top and a bottom, wherein said cartridge first end is at the bottom of said cartridge and wherein said cartridge second end is at the top of said cartridge, said cartridge having first and second sides extending between said ends, said passageway extending substantially from said first side to said second side, and said cartridge having a second wall extending between said sides and said ends and with said first wall defining said passageway, said first and second walls being closely spaced so that the flow of said liquid against said first wall is substantially laminar.

3. Apparatus as set forth in claim 2 wherein said passageway tapers towards said liquid outlet so that said passageway is narrowest at said outlet whereby air is purged from said passageway due to the liquid flowing from said inlet toward said outlet.

4. Apparatus as set forth in claim 1 wherein said receiver assembly for changing the temperature comprises a housing including a front wall and a back wall, said heat pump means being disposed between said housing walls and movable with respect to aid front wall between a first position in which the spacing therebetween is less than the thickness of said cartridge, and a second position wherein said cartridge is disposed between said first wall and said heat pump means.

5. Apparatus as set forth in claim 4 wherein said assembly further includes biasing means working against said back wall urging said heat pump means toward said first position.

6. Apparatus as set forth in claim 4 wherein said cartridge includes a second wall in registration with said first wall and defining therewith said passageway, said liquid inlet and said liquid outlet extending from said second wall away from said first wall, said housing front wall of said receiver assembly having a slot aligned with said inlet and outlet so that said cartridge can be moved between said heat pump means and said front wall without interference from said inlet and said outlet.

7. Apparatus as set forth in claim 4 wherein at least one of said cartridge and said heat pump means includes deflection means for moving said heat pump means toward said second position in response to incipient insertion of said cartridge into said housing.

8. Apparatus as set forth in claim 4 wherein said housing includes abutment means for limiting the extent of insertion of said cartridge into said housing.

9. Apparatus as set forth in claim 1 further comprising a plate on which said heat pump means is mounted.

10. A cartridge for reception into a receiver assembly for changing the temperature of an infusible liquid from a first temperature to a second predetermined temperature, said receiver assembly including a thermoelectric heat pump means for transferring heat to and absorbing heat from said cartridge, said heat pump being deflectable from a first position to a second position, said cartridge having an upper end and a lower end and comprising:
   a first wall formed of material having relatively good heat transfer properties;
   a second wall joined to said first wall and defining therewith a liquid passageway, said second wall being formed of material having relatively poor heat transfer properties;
   a liquid inlet communicating with said passageway adjacent said lower end and extending from said second wall away from said first wall;
   a liquid outlet communicating with said passageway adjacent said upper end; and
   deflection means for urging said heat pump means toward said second position in response to incipient insertion of said cartridge into said receiver assembly.

11. A disposable liquid cartridge for use with an apparatus for changing infusible liquids from a first temperature to a second temperature, said apparatus including a thermoelectric heat pump means for transferring heat to and absorbing heat from said cartridge, said cartridge forming a wide, thin, enclosed volume defining a flow path for an infusible liquid flowing therethrough, said cartridge comprising:
   a liquid inlet communicating with said enclosed volume and disposed toward the bottom of said cartridge;
   a liquid outlet communicating with said enclosed volume and disposed toward the top of said cartridge;
   a thin first cartridge plate;
   a second cartridge plate joined to said first plate to define said volume; and
   means for purging air bubbles from said liquid as said cartridge is filled with liquid.

12. A cartridge in accordance with claim 11 wherein said first cartridge plate is substantially flat.

13. A cartridge in accordance with claim 11 wherein said first cartridge plate is made of a material that is highly thermally conductive.

14. A cartridge in accordance with claim 11 wherein said first cartridge plate is made of a material that is highly thermally radiant.

15. A cartridge in accordance with claim 11 wherein said first plate is made of a material that is both highly thermally conductive and highly thermally radiant.

16. A cartridge in accordance with claim 15 wherein said first cartridge plate is black anodized aluminum.

17. A cartridge in accordance with claim 11 wherein said second wall is formed from a thermoplastic material.

18. A cartridge in accordance with claim 11 wherein said enclosed volume tapers to a minimum at one point downstream from the inlet within the cartridge whereby air bubbles are purged from blood as it fills the chamber.

19. A cartridge in accordance with claim 11 wherein said first cartridge plate has a raised rim around the periphery of said plate and a recessed central area whereby the inner surface of said recessed central area, the inner surface of said raised rim and the inner surface of said second plate define the enclosed volume of the cartridge.

20. A cartridge in accordance with claim 19 wherein said means for purging air bubbles is provided by a pair of rim extensions integral with the raised rim converging to narrow the flow path through said enclosed volume at at least one point between the liquid inlet and the liquid outlet.

21. A cartridge in accordance with claim 20 wherein the convergence of said rim extensions restricts the flow path at the liquid outlet.

22. A cartridge in accordance with claim 11 wherein the thin enclosed volume formed in said cartridge is between about 0.5 mm and about 2 mm thick.

23. A cartridge in accordance with claim 11 wherein the cartridge is between about 0.5 mm and about 3 mm thick.

24. An apparatus for varying the temperature of a transfusable liquid from the first temperature to a selected second desired temperature said apparatus comprising:
    a cartridge forming an enclosed volume for confining said liquid, said cartridge having a liquid inlet and liquid outlet, said cartridge having at least one wall formed of a material having good heat transfer properties;
    at least one thermoelectric heat pumping means for transferring heat to and absorbing heat from said cartridge, said heat pumping means being disposed in intimate thermal contact with at least one of said walls formed of a material having good heat transfer properties for changing the temperature of the transfusable liquid exiting the cartridge;
    temperature sensing means for determining the temperature of the liquid near said outlet; and
    thermal control means for regulating said thermoelectric heat pumping means in response to the liquid outlet temperature and maintaining the transfusable liquid at said second temperature.

25. A method for warming an infusible liquid from a first variable temperature to a second temperature comprising:
    providing a liquid cartridge having a liquid inlet and liquid outlet contiguous with a wide thin enclosed volume of relatively short liquid path length for confining an infusible liquid flowing therethrough, said cartridge having at least one thin high surface area wall made from a material with good thermal transfer properties;
    providing an infusible liquid flowing into a liquid cartridge inlet;
    providing heat to the liquid in the enclosed volume from at least one high surface area wall made of a material with good thermal transfer properties;
    providing heat to at least one high surface area wall at a rate proportional to the amount of heat absorbed by said liquid at said wall from at least one thermoelectric heat pumping means for transferring heat to and absorbing heat from said cartridge;
    sensing the temperature of the liquid near said liquid outlet;
    activating said thermoelectric heat pumping means when the sensed temperature is a predetermined temperature less than the second temperature;
    deactivating said thermoelectric heat pumping means when the sensed temperature is equal to the desired temperature, said deactivation of said thermoelectric heat pumping means causing substantially instantaneous thermal equilibrium between the cold and hot sides of said thermoelectric heat pumping means and drawing a small amount of heat from the liquid cartridge;
    providing a conduit attached to the liquid outlet for receiving the warmed blood, whereby the temperature of the blood at the liquid outlet is maintained at substantially the desired temperature.

* * * * *

UNITED STATES PATENT AND TRADEMARK OFFICE
CERTIFICATE OF CORRECTION

PATENT NO. : 5,125,069

DATED : June 23, 1992

INVENTOR(S) : Matthew O'Boyle

It is certified that error appears in the above-identified patent and that said Letters Patent is hereby corrected as shown below:

In Column 3, line 21, after the word "illustrated" insert the word --by--.

IN THE CLAIMS:

At Column 11, line 23 (Claim 1, line 16) after the word "transferring" insert the word --heat--.

At Column 11, line 24 (Claim 1, line 17) after the word "cartridge" insert a comma --,--.

At Column 11, line 46 (Claim 3, line 2) change "towards" to read --toward--.

At Column 11, line 54 (Claim 4, line 5) change "aid" to read --said--.

At Column 12, line 20 (Claim 10, line 6) after "pump" insert the word --means--.

UNITED STATES PATENT AND TRADEMARK OFFICE
CERTIFICATE OF CORRECTION

PATENT NO. : 5,125,069
DATED : June 23, 1992
INVENTOR(S) : Matthew O'Boyle

It is certified that error appears in the above-indentified patent and that said Letters Patent is hereby corrected as shown below:

Column 13, line 34 (claim 24, line 2) change "the" to read --a--

Signed and Sealed this

Seventh Day of December, 1993

Attest:

BRUCE LEHMAN

Attesting Officer

Commissioner of Patents and Trademarks